(12) United States Patent
Odori (10) Patent No.: US 12,357,262 B2
(45) Date of Patent: Jul. 15, 2025

(54) RADIOGRAPHIC IMAGING SYSTEM, RADIOGRAPHIC IMAGING APPARATUS, METHOD FOR CONTROLLING RADIOGRAPHIC IMAGING APPARATUS, AND STORAGE MEDIUM

(71) Applicant: CANON KABUSHIKI KAISHA, Tokyo (JP)

(72) Inventor: Junya Odori, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 248 days.

(21) Appl. No.: 18/332,497

(22) Filed: Jun. 9, 2023

(65) Prior Publication Data

US 2023/0414190 A1 Dec. 28, 2023

(30) Foreign Application Priority Data

Jun. 28, 2022 (JP) ................................ 2022-103659

(51) Int. Cl.
*A61B 6/00* (2024.01)
(52) U.S. Cl.
CPC .................................... *A61B 6/542* (2013.01)
(58) Field of Classification Search
CPC ......... A61B 6/542; A61B 6/548; A61B 6/563; A61B 6/56; A61B 6/566; A61B 6/545; A61B 6/54; A61B 2560/0266; A61B 2560/029; H05G 1/30; H05G 1/38; H05G 1/42; H05G 1/56
See application file for complete search history.

(56) References Cited

FOREIGN PATENT DOCUMENTS

JP 2013138829 A 7/2013
JP 2023062593 A * 5/2023 ............. A61B 6/542

* cited by examiner

*Primary Examiner* — Don K Wong
(74) *Attorney, Agent, or Firm* — Canon U.S.A., Inc. IP Division (57) ABSTRACT

A radiographic imaging system includes a control apparatus configured to control a radiation generation apparatus, and a radiographic imaging apparatus including a sensor unit configured to detect radiation emitted from the radiation generation apparatus and a communication unit configured to transmit, to the control apparatus, an irradiation stop signal to stop the radiation generation apparatus from emitting radiation based on a dose of the radiation detected by the sensor unit, wherein the communication unit transmits, to the control apparatus, a plurality of control signals as one set, each of the plurality of control signals including the irradiation stop signal, and wherein the control apparatus stops generation of radiation from the radiation generation apparatus based on the plurality of control signals.

20 Claims, 10 Drawing Sheets

RADIOGRAPHIC IMAGING SYSTEM, RADIOGRAPHIC IMAGING APPARATUS, METHOD FOR CONTROLLING RADIOGRAPHIC IMAGING APPARATUS, AND STORAGE MEDIUM

BACKGROUND

Field

The present disclosure relates to a radiographic imaging system, a radiographic imaging apparatus, and a method for controlling the radiographic imaging system.

Description of the Related Art

Radiographic imaging apparatuses with an automatic exposure control (AEC) function are known. The radiographic imaging apparatuses measure an amount of radiation during irradiation and can end the irradiation based on a result of the measurement. The radiographic imaging apparatuses monitor the amount of radiation by operating only pixels set for radiation detection at high speed during the irradiation.

Japanese Patent Application Laid-Open No. 2013-138829 discusses such a radiographic imaging apparatus that includes a dose detection unit in an imaging region of the radiographic imaging apparatus. The dose detection unit detects a dose of radiation having arrived at the imaging region.

Japanese Patent Application Laid-Open No. 2013-138829 discusses a technique for predicting a stop timing to stop a radiation generation apparatus from emitting radiation based on the dose detected by the dose detection unit and a preset target dose value. Japanese Patent Application Laid-Open No. 2013-138829 discusses a technique for issuing an irradiation stop timing notification to notify the radiation generation apparatus of an irradiation stop timing at a time point preceding the irradiation stop timing by a predetermined time considering a communication delay time. At this time, according to Japanese Patent Application Laid-Open No. 2013-138829, an average value for a communication path is used as the communication delay time, and the irradiation stop timing notification is repeated at predetermined intervals considering an occurrence of a communication failure.

Conventional techniques have an issue of accuracy in performing irradiation stop control to stop a radiation generation apparatus from emitting radiation. Specifically, in a case where a transmission dose rate of radiation transmitted through a subject increases, an exposure time decreases. In this case, with a conventional technique, an irradiation stop timing notification may not be issued in time, and an issue may arise that a cumulative dose of radiation exceeds a target dose value. Particularly, the communication delay time has different values at different time points, and in a case where it takes approximately several milliseconds for the cumulative dose of radiation to reach a threshold, a slight change in the communication delay time can cause a significant error in a final cumulative dose of radiation.

SUMMARY OF THE INVENTION

According to an aspect of the present disclosure, a radiographic imaging system includes a control apparatus configured to control a radiation generation apparatus, and a radiographic imaging apparatus including a sensor unit configured to detect radiation emitted from the radiation generation apparatus and a communication unit configured to transmit, to the control apparatus, an irradiation stop signal to stop the radiation generation apparatus from emitting radiation based on a dose of the radiation detected by the sensor unit, wherein the communication unit transmits, to the control apparatus, a plurality of control signals as one set, each of the plurality of control signals including the irradiation stop signal, and wherein the control apparatus stops generation of radiation from the radiation generation apparatus based on the plurality of control signals.

Further features will become apparent from the following description of exemplary embodiments with reference to the attached drawings.

DESCRIPTION OF THE EMBODIMENTS

The present exemplary embodiment is directed to performing irradiation stop control on a radiation generation apparatus with high accuracy.

According to an exemplary embodiment of the present disclosure, a communication unit transmits, to a control apparatus, a plurality of control signals as one set, each of the plurality of control signals including a irradiation stop signal, in a case where the control apparatus is to stop a radiation generation apparatus from emitting radiation based on the plurality of control signals.

This enables performing, for example, irradiation stop control on the radiation generation apparatus with high accuracy.

Various exemplary embodiments of the present disclosure will be described below with reference to the attached drawings. Similar components are provided with the same reference number(s) throughout the disclosure, and redundant descriptions thereof are omitted. The exemplary embodiments can be changed and/or combined as needed.

Figure 1:
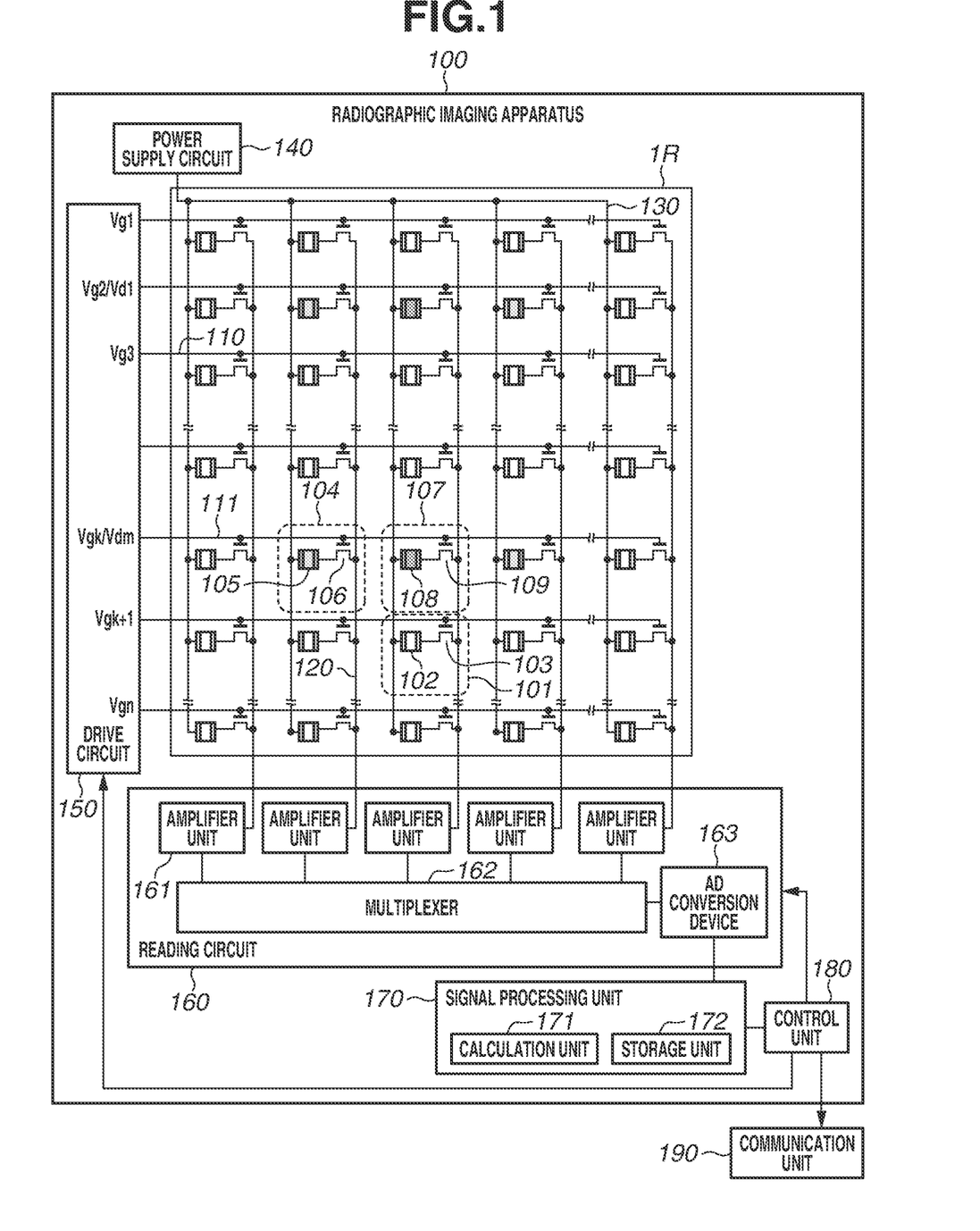
FIG. 1 is a diagram illustrating a configuration of a radiographic imaging apparatus according to an exemplary embodiment.

FIG. 1 illustrates an example of a configuration of a radiographic imaging apparatus 100 according to a first exemplary embodiment. The radiographic imaging apparatus 100 includes a plurality of pixels, a plurality of drive lines 110, and a plurality of signal lines 120. The plurality of pixels is arranged to form a plurality of rows and a plurality of columns in an imaging region IR. The plurality of drive lines 110 is arranged to correspond to the plurality of pixel rows, and each drive line 110 corresponds to one of the pixel rows. The plurality of signal lines 120 is arranged to correspond to the plurality of pixel columns, and each signal line 120 corresponds to one of the pixel columns.

The plurality of pixels includes a plurality of imaging pixels 101, one or more detection pixels 104, and one or more correction pixels 107. The plurality of imaging pixels 101 is used to acquire radiographic images. The detection pixel 104 is used to monitor an irradiation amount of radiation. The correction pixel 107 is used to correct the irradiation amount of radiation. The correction pixel 107 is lower in sensitivity to radiation than the detection pixel 104. Specifically, the imaging region IR including the plurality of pixels is a sensor unit configured to detect radiation 507 from a radiation generation apparatus 506 described below.

Each imaging pixel 101 includes a conversion element 102 and a switch element 103. The conversion element 102 converts radiation into an electric signal. The switch element 103 connects the corresponding signal line 120 and the conversion element 102 together. The detection pixel 104 includes a conversion element 105 and a switch element 106. The conversion element 105 converts radiation into an electric signal. The switch element 106 connects the corresponding signal line 120 and the conversion element 105 together.

The detection pixel 104 is arranged to be included in the row and column formed by the plurality of imaging pixels 101. The correction pixel 107 includes a conversion element 108 and a switch element 109. The conversion element 108 converts radiation into an electric signal. The switch element 109 connects the signal line 120 and the conversion element 108 together. The correction pixel 107 is arranged to be included in the row and column formed by the plurality of imaging pixels 101. In FIG. 1 and the subsequent drawings, the conversion element 102, the conversion element 105, and the conversion element 108 are cross-hatched differently from each other to discriminate between the imaging pixels 101, the detection pixel 104, and the correction pixel 107.

The conversion element 102, the conversion element 105, and the conversion element 108 can be formed by a scintillator that converts radiation into light and a photoelectric conversion element that converts light into an electric signal. In general, a scintillator is formed in the shape of a sheet to cover the imaging region IR and is shared by the plurality of pixels. The conversion element 102, the conversion element 105, and the conversion element 108 can also be formed by a conversion element that converts radiation directly into an electric signal.

The switch element 103, the switch element 106, and the switch element 109 can include, for example, a thin film transistor (TFT) with an active region formed by a semiconductor such as an amorphous silicon or a polycrystalline silicon.

A first electrode of the conversion element 102 is connected to a first main electrode of the switch element 103, and a second electrode of the conversion element 102 is connected to a bias line 130. Each bias line 130 extends in a column direction and is commonly connected to the second electrodes of the plurality of conversion elements 102 arranged in the column direction. The bias lines 130 receive a bias voltage Vs from a power supply circuit 140. A second main electrode of the switch element 103 of the imaging pixel 101 included in one column is connected to one signal line 120. A control electrode of the switch element 103 of one or more imaging pixels 101 included in one row is connected to one drive line 110.

The detection pixel 104 and the correction pixel 107 have a pixel structure similar to that of each imaging pixel 101 and are connected to the corresponding drive line 110 and the corresponding signal line 120. The detection pixel 104 and the correction pixel 107 are exclusively connected to the signal line 120. Specifically, no correction pixel 107 is connected to the signal line 120 to which the detection pixel 104 is connected. No detection pixel 104 is connected to the signal line 120 to which the correction pixel 107 is connected. Each imaging pixel 101 can be connected to the signal line 120 to which the detection pixel 104 or the correction pixel 107 is connected.

A drive circuit 150 is configured to supply a drive signal to a drive target pixel through the plurality of drive lines 110 based on a signal from a control unit 180. According to the present exemplary embodiment, the drive signal is a signal for turning on a switch element of the drive target pixel. A switch element of a pixel is turned on by a high-level signal and is turned off by a low-level signal. Thus, the high-level signal will be referred to as a "drive signal".

With the drive signal supplied to a pixel, signals accumulated in a conversion element of the pixel become ready to be read by a reading circuit 160. In a case where a drive line 110 is connected to at least one or more of the detection pixel 104 or the correction pixel 107, the drive line 110 is referred to as a "detection drive line 111".

The reading circuit 160 is configured to read signals from a plurality of pixels through the plurality of signal lines 120. The reading circuit 160 includes a plurality of amplifier units 161, a multiplexer 162, and an analog-digital conversion device (hereinafter, "AD conversion device") 163.

Each of the plurality of signal lines 120 is connected to the corresponding one of the plurality of amplifier units 161 of the reading circuit 160. One signal line 120 corresponds to one amplifier unit 161. The multiplexer 162 selects the plurality of amplifier units 161 in a predetermined order and supplies signals from the selected amplifier unit 161 to the AD conversion device 163. The AD conversion device 163 converts the supplied signals into digital signals and outputs the digital signals.

Signals read from the imaging pixels 101 are supplied to a signal processing unit 170, and the signal processing unit 170 performs calculation processing and/or storage processing on the supplied signals. Specifically, the signal processing unit 170 includes a calculation unit 171 and a storage unit 172, and the calculation unit 171 generates a radiographic image based on signals read from the imaging pixels 101 and supplies the generated radiographic image to the control unit 180.

Signals read from the detection pixel 104 and the correction pixel 107 are supplied to the signal processing unit 170, and the calculation unit 171 of the signal processing unit 170 performs calculation processing and/or storage processing on the supplied signals. Specifically, the signal processing unit 170 outputs irradiation information about radiation on the radiographic imaging apparatus 100 based on the signals read from the detection pixel 104 and the correction pixel 107. For example, the signal processing unit 170 detects radiation irradiation on the radiographic imaging apparatus 100 and determines an irradiation amount and/or a cumulative irradiation amount of radiation.

The control unit 180 controls the drive circuit 150 and the reading circuit 160 based on the information from the signal processing unit 170. The control unit 180 controls, for example, a start and an end of exposure (accumulation of charges corresponding to emitted radiation by the imaging pixels 101) based on the information from the signal processing unit 170. The control unit 180 can be formed by a general-purpose processing circuit such as a microprocessor or a dedicated processing circuit such as an application specific integrated circuit (ASIC). In a case where the control unit 180 is formed by a general-purpose processing circuit, the control unit 180 can also include a memory.

In order to set an irradiation amount of radiation, the control unit 180 controls the drive circuit 150 to only scan the detection drive line 111 so that only signals from the detection pixel 104 and the correction pixel 107 are to be read. Next, the control unit 180 controls the reading circuit 160 to read signals from columns corresponding to the detection pixel 104 and the correction pixel 107 and outputs the read signals as information indicating an irradiation amount of radiation. The foregoing operations enable the radiographic imaging apparatus 100 to acquire irradiation information about the detection pixel 104 during irradiation.

A communication unit 190 is controlled by the control unit 180 and has a function of performing communication between the radiographic imaging apparatus 100 and external devices. The communication unit 190 that realizes communication of a desired method or standard such as wired communication or wireless communication can be used, and the communication is not limited to a specific standard. A plurality of communication units 190 can be included to support a plurality of communication standards.

Figure 2:
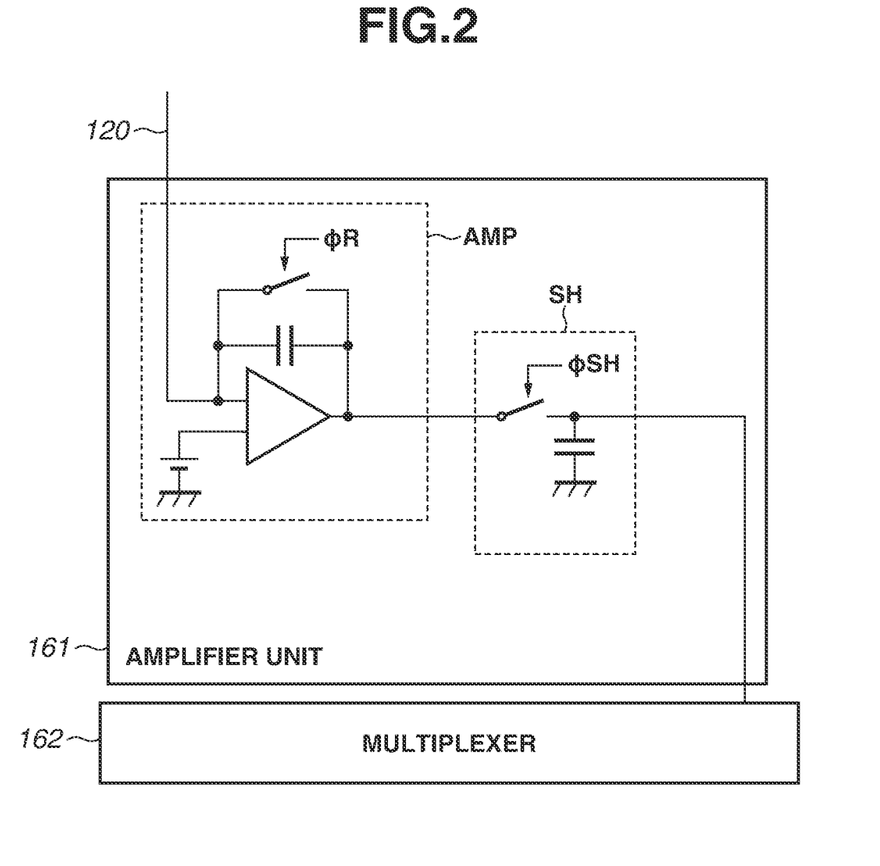
FIG. 2 is a diagram illustrating a configuration of an amplifier unit according to an exemplary embodiment.

FIG. 2 illustrates an example of a detailed circuit structure of the amplifier units 161. Each amplifier unit 161 includes a differential amplifier circuit AMP and a sample-and-hold circuit SH. The differential amplifier circuit AMP amplifies signals that emerge on the signal line 120, and outputs amplified signals. The control unit 180 can reset a potential of the signal line 120 by supplying a signal φR to a switch element of the differential amplifier circuit AMP.

The output from the differential amplifier circuit AMP can be stored by the sample-and-hold circuit SH. The control unit 180 causes the sample-and-hold circuit SH to store a signal by supplying a signal φSH to a switch element of the sample-and-hold circuit SH. The signal stored by the sample-and-hold circuit SH is read by the multiplexer 162.

Figure 3:
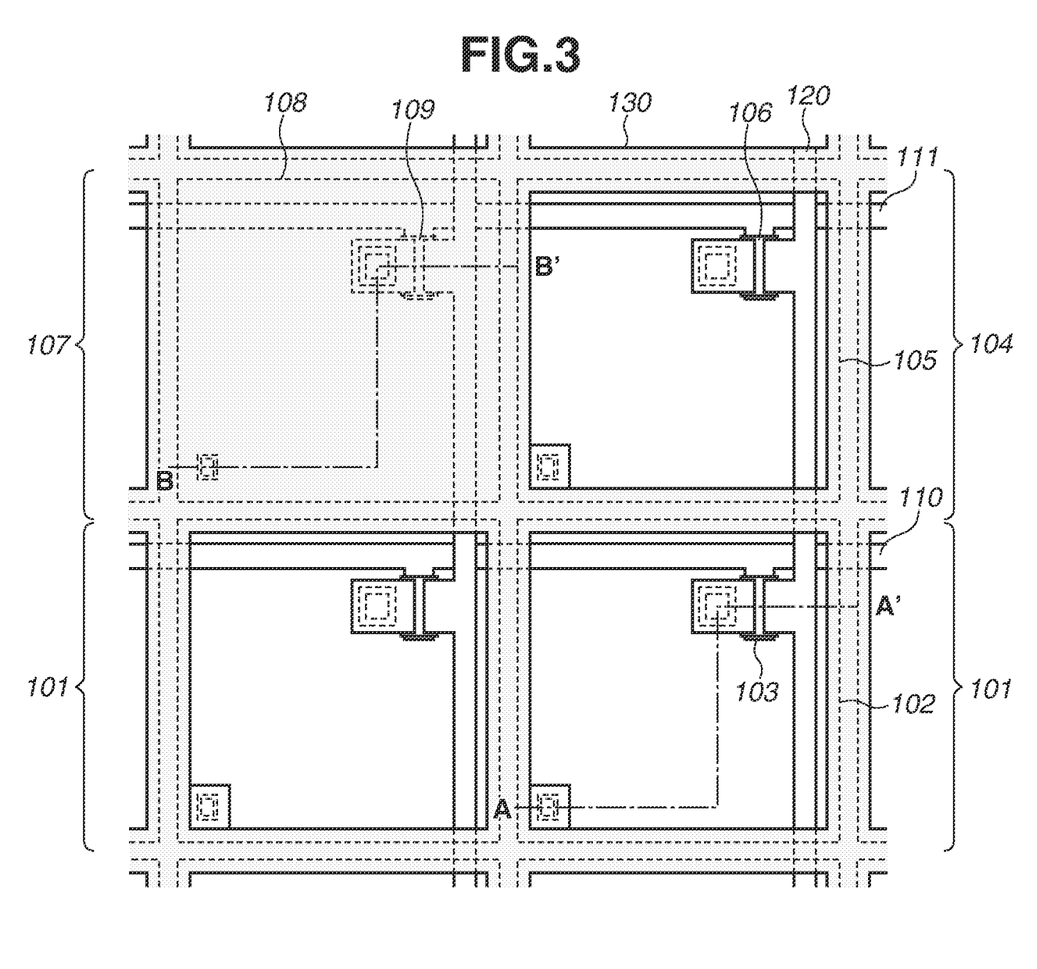
FIG. 3 is a view illustrating a structure of each pixel according to an exemplary embodiment.

A pixel structure of the radiographic imaging apparatus 100 will be described below with reference to FIGS. 3, 4A, and 4B. FIG. 3 is a view illustrating a structure of the imaging pixels 101, the detection pixel 104, and the correction pixel 107 of the radiographic imaging apparatus 100. The view is equivalent to an orthographic projection to a plane parallel to the imaging region IR of the radiographic imaging apparatus 100. As indicated by cross-hatching, a metal layer is provided on the conversion element 108 of the correction pixel 107, and the conversion element 108 is shielded from light by the metal layer.

Figure 4A:
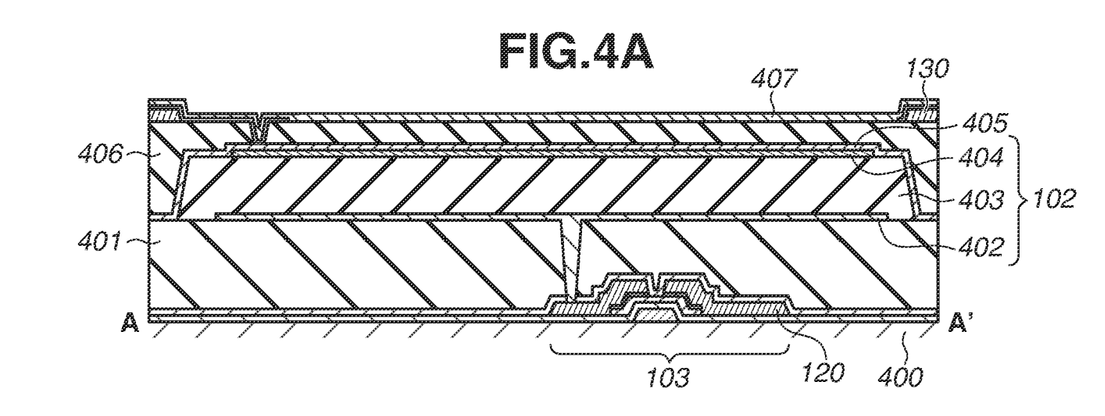
FIGS. 4A and 4B are cross-sectional views illustrating a structure of each pixel according to an exemplary embodiment.

FIG. 4A is a cross-sectional view illustrating the imaging pixel 101 along line A-A' in FIG. 3. A cross-sectional view of the detection pixel 104 is similar to the cross-sectional view of the imaging pixel 101. The switch element 103 is provided on a support substrate 400 such as a glass substrate. The support substrate 400 has insulating properties. The switch element 103 can be a TFT.

An interlayer insulation layer 401 is on the switch element 103. The conversion element 102 is on the interlayer insulation layer 401. The conversion element 102 is a photoelectric conversion element capable of converting light into an electric signal. The conversion element 102 includes, for example, an electrode 402, a PIN photodiode 403, and an electrode 404. The conversion element 102 can be formed by a magnetic image sensor (MIS) instead of being a PIN-type photodiode.

A protection film 405, an interlayer insulation layer 406, a bias line 130, and a protection film 407 are arranged on the conversion element 102 on top of one another. A planarization film (not illustrated) and a scintillator (not illustrated) are on the protection film 407. The electrode 404 is connected to the bias line 130 via a contact hole. Indium tin oxide (ITO) having light transmission properties is used as a material of the electrode 404, and the electrode 404 transmits light converted from radiation by the scintillator (not illustrated).

Figure 4B:
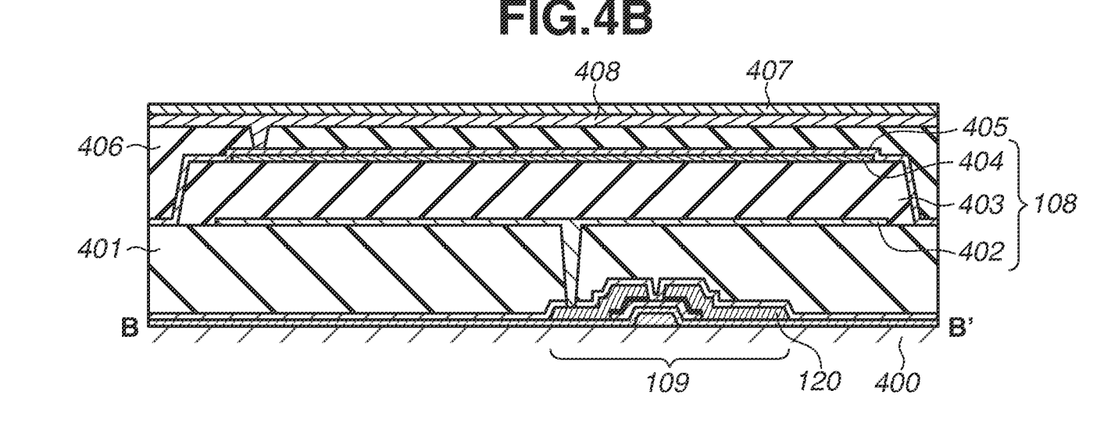

FIG. 4B is a cross-sectional view illustrating the correction pixel 107 along line B-B' in FIG. 3. The correction pixel 107 is different from the imaging pixel 101 and the detection pixel 104 in that the conversion element 108 is covered with a light shielding member 408. The rest of the correction pixel 107 can be the same as those of the imaging pixel 101 and the detection pixel 104. The light shielding member 408 is formed by, for example, a metal layer of the same layer as the bias line 130. Since the conversion element 108 of the correction pixel 107 is covered with the light shielding member 408, the correction pixel 107 is significantly lower in sensitivity to radiation than the imaging pixel 101 and the detection pixel 104. Charges accumulated in the conversion element 108 of the correction pixel 107 may not necessarily bet caused by radiation.

Figure 5:
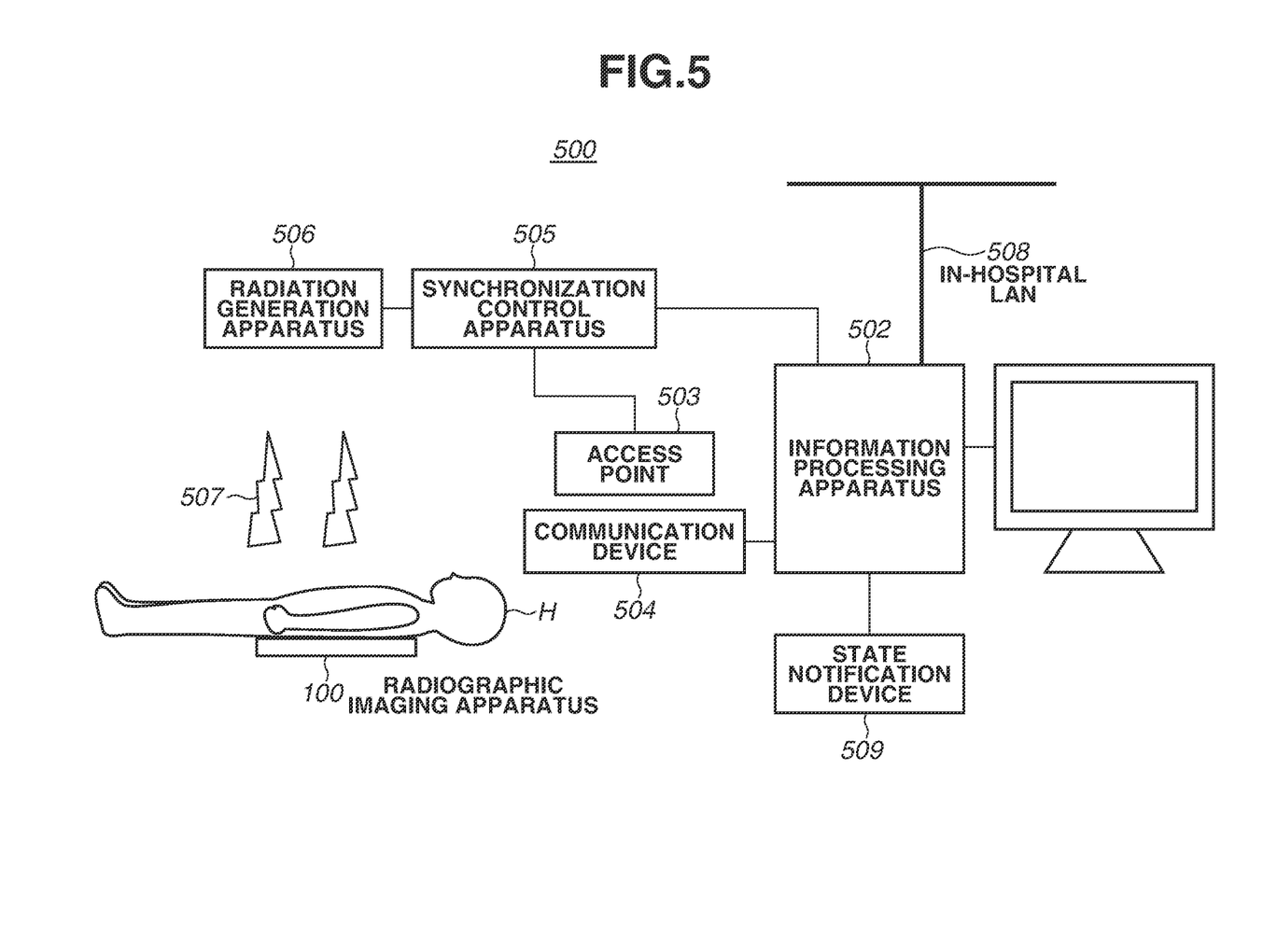
FIG. 5 is a diagram illustrating an example of a configuration of a radiographic imaging system according to an exemplary embodiment.

FIG. 5 illustrates an example of a configuration of a radiographic imaging system 500 including the radiographic imaging apparatus 100. The radiographic imaging system 500 includes, in addition to the radiographic imaging apparatus 100, an information processing apparatus 502, an access point 503, a communication device 504, a synchronization control apparatus 505, and the radiation generation apparatus 506.

The radiographic imaging apparatus 100 captures a radiographic image based on the radiation 507 transmitted through a subject H. The radiation 507 incident on the radiographic imaging apparatus 100 is converted into charges. The charges are processed as image data, and the image data is transmitted to the information processing apparatus 502.

The information processing apparatus 502 is a control apparatus realized by a publicly-known technique such as a general-purpose computer and includes a display unit, an input unit, and a control unit. The information processing apparatus 502 performs image processing for correction, storage, and/or display on the image data received from the radiographic imaging apparatus 100. Functions of the image processing can be performed partially or entirely by the radiographic imaging apparatus 100.

The information processing apparatus 502 displays a radiographic image to an operator and prompts the operator to perform imaging via the display unit. The information processing apparatus 502 has a function that the operator inputs imaging condition instructions using the input unit. The control unit of the information processing apparatus 502 has a function of comparing an acquired signal intensity and a threshold, a function of responding to a connection request, and a function of transmitting information such as wireless communication described below for performing communication using a wireless communication unit.

The access point 503 is a device that relays radio waves for wirelessly communicating information between the radiographic imaging apparatus 100 and the information processing apparatus 502. The control unit 180 of the radiographic imaging apparatus 100 controls the communication unit 190 and performs wireless communication. While the access point 503 is connected to the information processing apparatus 502 via the synchronization control apparatus 505 in FIG. 5, the access point 503 can be connected directly to the information processing apparatus 502.

The communication device 504 is a device that is connected to the information processing apparatus 502 and transmits and receives radio waves for wirelessly performing near-field communication between the radiographic imaging apparatus 100 and the information processing apparatus 502. For example, the communication device 504 is a dongle connected to the information processing apparatus 502 via a universal serial bus (USB) interface. The communication device 504 is a device that supports at least one of Bluetooth® Basic Rate/Enhanced Data Rate (BR/EDR) or Bluetooth® Low Energy (BLE) standards.

The communication device 504 can be a radio frequency identifier (RFID) device that communicates information with tags including identification (ID) information embedded therein via near-field wireless communication using an electromagnetic field or radio waves. A communication method of RFID can be either an electromagnetic induction method or a radio wave method. The communication device 504 can have an access point function.

While an example where the communication device 504 is connected to the information processing apparatus 502 is described above and illustrated in FIG. 5, the present exemplary embodiment is not limited to this example. The communication device 504 can be connected to another apparatus of the radiographic imaging system 500 such as the radiation generation apparatus 506. A device included in advance in the radiographic imaging system 500 can be used in place of the communication device 504.

A state notification device 509 as a unit for providing notifications to the operator is connected to the information processing apparatus 502. The state notification device 509 notifies the operator of a current state of the radiographic imaging apparatus 100 and/or an end of a specific process based on information about the radiographic imaging apparatus 100 that is received from the radiographic imaging apparatus 100 via the access point 503 or from the communication device 504.

A light emitting member such as a light emitting diode (LED) is used as the state notification device 509, and a plurality of lighting patterns is associated with current states of the radiographic imaging apparatus 100 in advance. The state notification device 509 provides notifications to the operator using the associated lighting patterns. The state notification device 509 can use a sound source such as a speaker. In this case, buzzer sound patterns are associated with the current states of the radiographic imaging apparatus 100 in advance, and the state notification device 509 provides notifications to the operator using the associated buzzer sound patterns. The foregoing forms can be used in combination.

While an example where the state notification device 509 is connected to the information processing apparatus 502 is described above, a device such as a display and a speaker of the information processing apparatus 502 can be used in place of the state notification device 509.

The synchronization control apparatus 505 includes a circuit that mediates communication, and monitors states of the radiographic imaging apparatus 100 and the radiation generation apparatus 506. For example, the synchronization control apparatus 505 controls the emission of the radiation 507 from the radiation generation apparatus 506 and the imaging of the subject H by the radiographic imaging apparatus 100. The synchronization control apparatus 505 can include a built-in hub for connecting a plurality of network devices.

In order to generate the radiation 507 such as X-rays, the radiation generation apparatus 506 includes, for example, a radiation tube that accelerates electrons at high voltage and causes the accelerated electrons to collide with an anode. While X-rays are generally used as the radiation 507, α-rays, β-rays, γ-rays, or neutron rays can be used as the radiation 507.

An in-hospital local area network (in-hospital LAN) 508 is a local area network located in a hospital and has a function of transmitting and receiving radiographic images captured by the radiographic imaging system 500 to and from various locations in the hospital.

In the radiographic imaging system 500 illustrated in FIG. 5, the subject H being a patient is irradiated with the radiation 507 emitted from the radiation generation apparatus 506. The radiographic imaging apparatus 100 generates a radiographic image based on the radiation 507 transmitted through the subject H.

The radiographic imaging system 500 can perform synchronous imaging and non-synchronous imaging. The synchronous imaging is an imaging method where the radiographic imaging apparatus 100 and the radiation generation apparatus 506 communicate electric synchronization signals via the synchronization control apparatus 505 to synchronize a timing to emit radiation with a timing to capture an image.

The non-synchronous imaging is an imaging method where the radiographic imaging apparatus 100 starts imaging on detection of incident radiation without communicating electric synchronization signals between the radiographic imaging apparatus 100 and the radiation generation apparatus 506. In the non-synchronous imaging, the radiographic imaging apparatus 100 can transfer a radiographic image each time imaging is performed, or the radiographic imaging apparatus 100 can store a captured image in the radiographic imaging apparatus 100 without transferring the image each time imaging is performed.

The radiographic imaging system 500 can perform imaging using imaging conditions under which images are generally captured in radiographic imaging, such as fluoroscopic imaging, continuous imaging, still-image imaging, digital subtraction angiography (DSA) imaging, roadmap imaging, programmed imaging, tomographic imaging, and tomosynthesis imaging.

Various function settings are set for the radiographic imaging system 500, such as an imaging framerate, a tube voltage, a tube current, a sensor reading area, a sensor driving/binning setting, a collimator aperture setting, a radiation window width, and a setting of whether to accumulate captured radiographic images in the radiographic imaging apparatus 100. Settings of functions such as automatic voltage control (auto dose control (ADC)) and automatic exposure control (auto exposure control (AEC)) are set for the radiographic imaging system 500.

A dose, an upper limit exposure time (ms), a tube current (mA), a tube voltage (kV), and a region-of-interest (ROI)

that is a region to monitor radiation are input to the information processing apparatus 502 via an input apparatus of the information processing apparatus 502. In a case where an exposure switch of the radiation generation apparatus 506 is operated, the information processing apparatus 502 transmits a start request signal to the radiographic imaging apparatus 100. The start request signal is a signal that is a request to start irradiation.

Upon receipt of the start request signal, the radiographic imaging apparatus 100 starts preparations to receive irradiation with radiation. In a case where the preparations are completed, the radiographic imaging apparatus 100 transmits a ready-to-start signal to the radiation generation apparatus 506 via the access point 503 or the communication device 504. The ready-to-start signal is a signal notifying that irradiation can be started. Upon receipt of the ready-to-start signal, the radiation generation apparatus 506 starts emitting the radiation 507.

In a case where the value of the cumulative dose of radiation reaches the threshold, the radiographic imaging apparatus 100 transmits an irradiation stop signal to the radiation generation apparatus 506 via the access point 503 or the communication device 504. The irradiation stop signal is a signal that is a request to stop irradiation. Upon receipt of the irradiation stop signal, the radiation generation apparatus 506 stops emitting the radiation 507.

The threshold for the dose is set by, for example, the control unit 180 based on an input dose value, a radiation intensity, a communication delay between units, and a processing delay. In a case where a radiation exposure time reaches the input upper limit exposure time, the radiation generation apparatus 506 can stop emitting radiation even if no irradiation stop signal has been received.

After the irradiation is stopped, the radiographic imaging apparatus 100 sequentially scans the drive lines 110 (the drive lines 110 other than the detection drive line 111) to which only the imaging pixels 101 are connected, and the reading circuit 160 reads image signals from the imaging pixels 101, whereby the radiographic imaging apparatus 100 acquires a radiographic image.

Charges accumulated in the detection pixel 104 are read during irradiation, and the correction pixel 107 is shielded from light, so that signals from the detection pixel 104 and the correction pixel 107 cannot be used in forming a radiographic image.

Thus, the signal processing unit 170 of the radiographic imaging apparatus 100 interpolates pixel values at positions of the detection pixel 104 and the correction pixel 107 by performing interpolation processing using pixel values of the imaging pixels 101 neighboring the detection pixel 104 and the correction pixel 107.

An example of operations of the radiographic imaging apparatus 100 will be described below with reference to FIG. 6. The operations are performed by the control unit 180 controlling the drive circuit 150 and the reading circuit 160 and the signal processing unit 170 in cooperation with each other. The operations enable setting of an amount of radiation to be emitted to the radiographic imaging apparatus 100.

Figure 6:
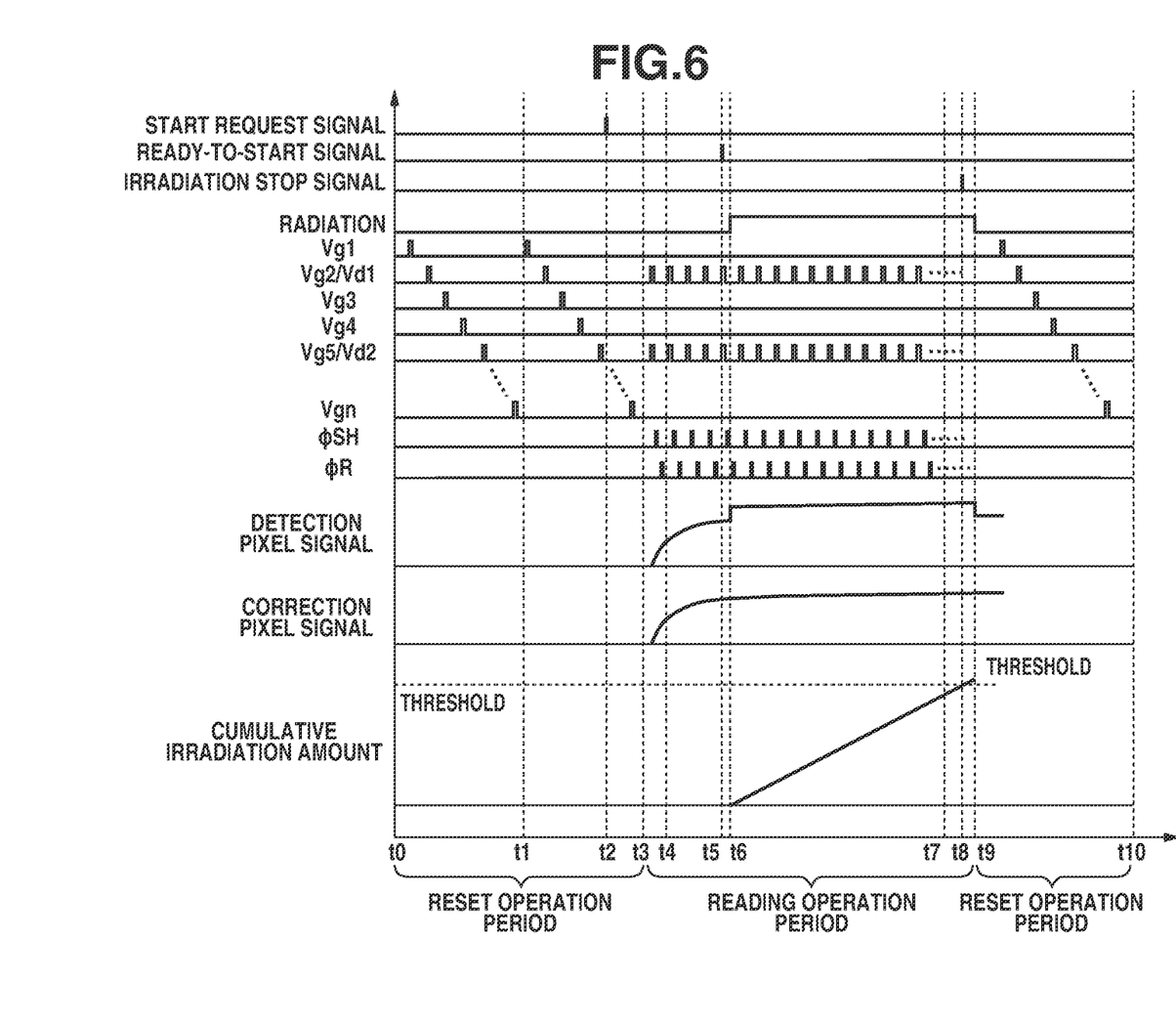
FIG. 6 is a diagram illustrating an example of operations of a radiographic imaging system according to an exemplary embodiment.

In FIG. 6, "RADIATION" indicates whether the radiographic imaging apparatus 100 is being irradiated with radiation. In a case where "RADIATION" is low, the radiographic imaging apparatus 100 is not being irradiated with radiation, whereas in a case where "RADIATION" is high, the radiographic imaging apparatus 100 is being irradiated with radiation.

"Vg1" to "Vgn" indicate drive signals supplied from the drive circuit 150 to the plurality of drive lines 110. "Vgk" corresponds to the drive line 110 of the kth row (k=1, . . . , the total number of drive lines). As described above, part of the plurality of drive lines 110 is also referred to as "detection drive line 111". The jth detection drive line 111 is denoted by "Vdj" (j=1, . . . , the total number of detection drive lines).

φSH indicates a level of a signal supplied to the sample-and-hold circuit SH of the amplifier unit 161, and φR indicates a level of a signal supplied to the differential amplifier circuit AMP of the amplifier unit 161. "Detection pixel signal" indicates a value of a signal read from the detection pixel 104. "Correction pixel signal" indicates a value of a signal read from the correction pixel 107. "Cumulative irradiation amount" indicates a cumulative value of radiation emitted to the radiographic imaging apparatus 100. A method for setting the cumulative value will be described below.

At time t0, the control unit 180 starts a reset operation to reset a plurality of pixels. The reset operation is an operation of removing charges accumulated in a conversion element of a pixel and, specifically, an operation of supplying a drive signal to the drive line 110 to change a switch element of each pixel to a conductive state. The control unit 180 resets each pixel connected to the drive line 110 of the first row by controlling the drive circuit 150.

The control unit 180 then resets each pixel connected to the drive line 110 of the second row.

The control unit 180 repeats the foregoing operation to the drive line 110 of the last row. At time t1, after the reset operation on the drive line 110 of the last row is ended, the control unit 180 repeats the reset operation starting from the drive line 110 of the first row.

At time t2, the control unit 180 receives a start request signal from the information processing apparatus 502. Upon the receipt of the start request signal, the control unit 180 performs the reset operation to the last row and then ends the reset operation. The control unit 180 can end the reset operation before performing the reset operation to the last row and can proceed to a next process.

For example, in a case where the control unit 180 receives a start request signal while performing the reset operation on the drive line 110 of the kth row, the control unit 180 can proceed to the next process without performing the reset operation on the drive lines 110 of the k+1th and subsequent rows. In this case, the driving for acquiring a radiographic image can be adjusted and/or image processing can be performed on the radiographic image to reduce a gap that may occur in the radiographic image.

At time t3, the control unit 180 starts a setting operation to set an amount of radiation emitted to the radiographic imaging apparatus 100. In the setting operation, the control unit 180 repeatedly performs a reading operation of reading from the detection pixel 104 and the correction pixel 107. Among the plurality of times of reading operations, one or more reading operations performed in the first half are performed to set a correction value, whereas the repeated reading operations in the last half are performed to continuously set an amount of radiation at each time point.

The reading operation is performed on the detection drive line 111 and is not performed on the other drive lines 110. Specifically, the drive circuit 150 supplies a drive signal to each drive line 110 (i.e., the detection drive line 111) connected to at least one of the detection pixel 104 and the correction pixel 107 among the plurality of drive lines 110.

The drive circuit 150, however, does not supply a drive signal to each drive lines 110 connected to neither the detection pixel 104 nor the correction pixel 107 among the plurality of drive lines 110. The drive circuit 150 simultaneously supplies a drive signal to the drive lines 110 connected to at least one of the detection pixel 104 and the correction pixel 107 among the plurality of drive lines 110. Consequently, signals from a plurality of pixels connected to the same signal line 120 are combined together and read by the reading circuit 160. Since the detection pixel 104 and the correction pixel 107 are exclusively connected to the signal lines 120, the reading circuit 160 can separately read signals of pixels of different sensitivities.

In one reading operation, the control unit 180 performs the operations of time t3 to time t4. Specifically, the control unit 180 temporarily supplies a drive signal to one or more detection drive lines 111. Thereafter, the control unit 180 temporarily changes the signal φSH to a high level, whereby the signals read from the pixels through the signal line 120 by the reading circuit 160 are held by the sample-and-hold circuit SH.

The control unit 180 then temporarily changes the signal φR to a high level, whereby the reading circuit 160 (specifically, the differential amplifier circuit AMP of the amplifier unit 161 of the reading circuit 160) is reset. In a case where a region-of-interest is set in the imaging region IR, signals from the detection pixel 104 that is not included in the region-of-interest do not have to be read.

The control unit 180 performs the reading operation a predetermined number of times in order to set a correction value. The predetermined number of times is greater than or equal to one.

The signal processing unit 170 sets a correction value Od based on signals read from the detection pixel 104 by the predetermined number of times of the reading operation and a correction value Oc based on signals read from the correction pixel 107 by the predetermined number of times of the reading operation.

The setting of the correction value Od will be described in detail below. In a case where the predetermined number of times is one, one signal is read from the detection pixel 104, so that the signal processing unit 170 sets a value of the signal as the correction value Od. In a case where the predetermined number of times is more than one, the signal processing unit 170 calculates an average value of the plurality of read signals and sets the calculated average value as the correction value Od. Another statistical value can be used in place of the average value. Similarly, the correction value Oc is set based on signals read from the correction pixel 107. The signal processing unit 170 stores the correction values Od and Oc set as described above in the storage unit 172 for use in subsequent processes.

After the reading operation ends once or more than once, at time t5, the control unit 180 transmits a ready-to-start signal to the radiation generation apparatus 506. The above-described setting of the correction values Od and Oc can be performed before or after the transmission of the ready-to-start signal. After transmitting the ready-to-start signal, the control unit 180 repeatedly performs the reading operation. The signal processing unit 170 measures an irradiation amount of radiation DOSE for each reading operation and determines whether a cumulative value of the irradiation amount of radiation DOSE exceeds the threshold. At time t6 after time t5, irradiation is started.

In a case where the cumulative irradiation amount reaches the threshold at time t8, the control unit 180 transmits an irradiation stop signal to the synchronization control apparatus 505. Upon receipt of the irradiation stop signal, the synchronization control apparatus 505 performs irradiation stop control to stop the radiation generation apparatus 506 from emitting radiation.

Instead of transmitting the irradiation stop signal at time t8, the control unit 180 can estimate time t8 at which the cumulative irradiation amount is to reach the threshold, and can transmit an irradiation stop signal at the estimated time t8. For example, an estimated transmission time t7 is calculated by adding a communication delay time until a signal from the communication unit 190 arrives at the synchronization control apparatus 505 to a predicted time of estimated time t8 at which the cumulative irradiation amount reaches the threshold, and an irradiation stop signal can be transmitted at the estimated transmission time t7. At time t9, the radiation generation apparatus 506 stops emitting radiation based on the irradiation stop control by the synchronization control apparatus 505.

After the irradiation is ended at time t9, the control unit 180 performs the reset operation on the plurality of pixels until time t10 similarly to time t0.

Figure 7:
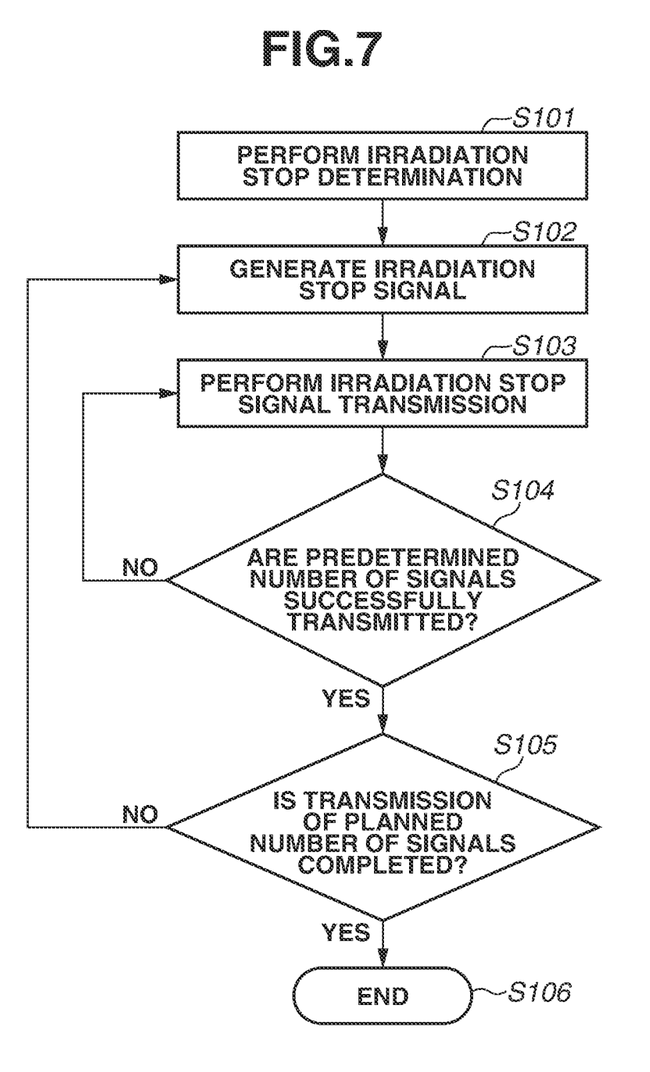
FIG. 7 is a diagram illustrating an example of a flow of transmitting an irradiation stop signal according to an exemplary embodiment.

Next, an example of a flow in which the control unit 180 of the radiographic imaging apparatus 100 determines to transmit an irradiation stop signal and transmits an irradiation stop signal will be described below with reference to FIG. 7.

In step S101, the control unit 180 performs irradiation stop determination based on the cumulative irradiation amount and the communication delay time.

In step S102, the control unit 180 generates a control signal including an irradiation stop signal. At this time, an additional signal can be added to the irradiation stop signal. For example, the additional signal can be identification information indicating the inclusion of the irradiation stop signal to facilitate filtering processing at a receiving end.

The additional signal can be transmission order information about consecutive numbers given to a series of signals to be transmitted so that the synchronization control apparatus 505 can estimate a situation of a communication environment upon receipt of the signals. At this time, in a case where the transmission order is reversed, the synchronization control apparatus 505 can assume that the order is changed due to a delay on the communication path, or in a case where there is an omission in the consecutive numbers, the synchronization control apparatus 505 can assume that a packet loss occurs during the transmission.

The additional signal can be time information so that a level of a communication delay can be estimated by comparing time information stored in the synchronization control apparatus 505 and the time information of the additional signal. The additional signal can be dose information calculated by the calculation unit 171 so that a dose at a current time point can be acquired.

The additional signal can be information indicating a separate imaging identifier (imaging ID) for each imaging operation to discriminate between imaging operations. In this case, the imaging IDs are desirably shared in advance with the synchronization control apparatus 505. This enables the synchronization control apparatus 505 to determine whether to perform irradiation stop control on the radiation generation apparatus 506 in current imaging in a case where an irradiation stop signal transmitted during the previous imaging and delayed due to a communication delay is received by the synchronization control apparatus 505.

The additional signal can be dummy data. For example, adjusting a size using dummy data is suitable for a communication device that prioritizes transmission of a signal containing data of a predetermined size or larger. In this case, the data size is desirably a value to avoid packet fragmentation under currently-used standards.

For example, a maximum data size to avoid Internet Protocol (IP) fragmentation under Ethernet is generally 1500 bytes. In a case where transmission is to be performed using a user datagram protocol (UPD) as a protocol, since an IP header and a UPD header in combination use 28 bytes, a substantial maximum data size is 1472 bytes. Fragmentation is avoided because the number of packets to be used to restore one packet increases as a result of fragmentation and a frequency of an occurrence of a delay such as re-transmission due to a packet loss increases.

A plurality of control signals including an irradiation stop signal can be transmitted as one set. The number of signals to be transmitted is to be set by calculating an actual transfer time and considering a response time requested by communication of control commands between the radiographic imaging apparatus 100 and other devices in the radiographic imaging system 500. The actual transfer time is calculated by dividing, by an effective communication speed, a result of multiplying a data size by the number of pieces of data to be transmitted.

For example, in a communication environment where the effective communication speed is 100 Mbps, an actual transfer time of about 1.2 ms is needed to transmit ten signals with a data size of 1500 bytes. During this time, a communication band is occupied, and other communications of control commands or the like can be affected. The number of control signals to be transmitted at one time is desirably 1000 or less.

Usages of the additional signals are not limited to those described herein according to the present exemplary embodiment, and any additional signals can be used in combination. For example, in a case where a plurality of irradiation stop signals is to be transmitted in one transmission, the additional signal to be added to each of the plurality of irradiation stop signals can be the same as the additional signal to be added to each of the other irradiation stop signals. The additional signal to be added to each of the plurality of irradiation stop signals can be partially or entirely different from the additional signal to be added to each of the other irradiation stop signals. Not adding an additional signal can be selected.

The additional signals can be used in desired control at the receiver end, and an estimation result and/or a control result added thereto can be transmitted together with a receipt response signal to the radiographic imaging apparatus 100, which is the transmitter end.

In step S103, the control signal including the generated irradiation stop signal is transmitted to the access point 503 until the number of control signals to be transmitted reaches the predetermined number of signals. The signal transmission is performed based on, for example, the Institute of Electrical and Electronics Engineers (IEEE) 802.11 standards for wireless communication.

Since wireless communication is half-duplex communication, in a case where, for example, another wireless device (not illustrated) simultaneously transmits a radio wave over a frequency band in use, a radio wave collision can occur, and the access point 503 can fail to receive the irradiation stop signal normally. In this case, no response signal (ACK) is returned from the access point 503 to the communication unit 190.

Upon receipt of the first one of the plurality of irradiation stop signals transmitted from the radiographic imaging apparatus 100, the synchronization control apparatus 505 performs irradiation stop control to stop the radiation generation apparatus 506 from emitting the radiation 507.

In step S104, the communication unit 190 determines whether the predetermined number of signals are successfully transmitted to the access point 503 by checking a response signal (ACK). In a case where no response signal (ACK) is returned, the control signal transmission in step S103 is repeated until the number of transmitted signals reaches the predetermined number of signals.

In step S105, whether the transmission of the planned number of signals is completed is determined. In a case where the number of transmitted signals has reached the planned number of signals (YES in step S105), the processing proceeds to step S106 and exits the flowchart. In a case where the number of transmitted signals has not reached the planned number of signals (NO in step S105), the sequence from step S102 of generating a control signal is repeated. At this time, additional signals that change over time such as time information and cumulative dose are desirably updated in generating a control signal in step S102.

The foregoing operations enable the radiographic imaging apparatus 100 to transmit the planned number of control signals with a desired additional signal added to an irradiation stop signal as one set while updating the signals at desired timings. This prevents a communication delay in the irradiation stop control to stop the radiation generation apparatus 506 from emitting the radiation 507 based on the irradiation stop signal from the radiographic imaging apparatus 100, so that the accuracy of the irradiation stop control improves.

The transmission of "a plurality of signals as one set" is realized by, for example, transmitting the signals simultaneously from a plurality of antennas using a multiple input multiple output (MIMO) technique. The transmission can also be realized by combining a plurality of data frames together by frame aggregation, transmitting the combined data frames, and receiving response signals collectively using Block ACK.

The transmission can also be realized based on a carrier sense multiple access with collision avoidance (CSMA/CA) method. The radiographic imaging apparatus 100 can be configured to select a form of transmitting a plurality of control signals as one set as described above or a form of transmitting one control signal per transmission.

In order to transmit an irradiation stop signal from the communication unit 190 without a delay in step S103, it is desirable to not retain a transmission packet queue in the communication unit 190 at a previous timing before the irradiation stop signal transmission. The previous timing refers to a timing from a point where the radiation generation apparatus 506 starts emitting the radiation 507 to a point where the irradiation stop determination is performed by the control unit 180 based on the cumulative irradiation amount and the communication delay time in step S101. During this timing, the communication unit 190 desirably stops transmitting signals to the synchronization control apparatus 505 via the access point 503.

In a case where the radiographic imaging apparatus 100 receives a control command requesting a response from the synchronization control apparatus 505, from the point of view of promptly performing a control response, a response signal is desirably transmitted from the communication unit 190 even during irradiation with the radiation 507.

Figure 8:
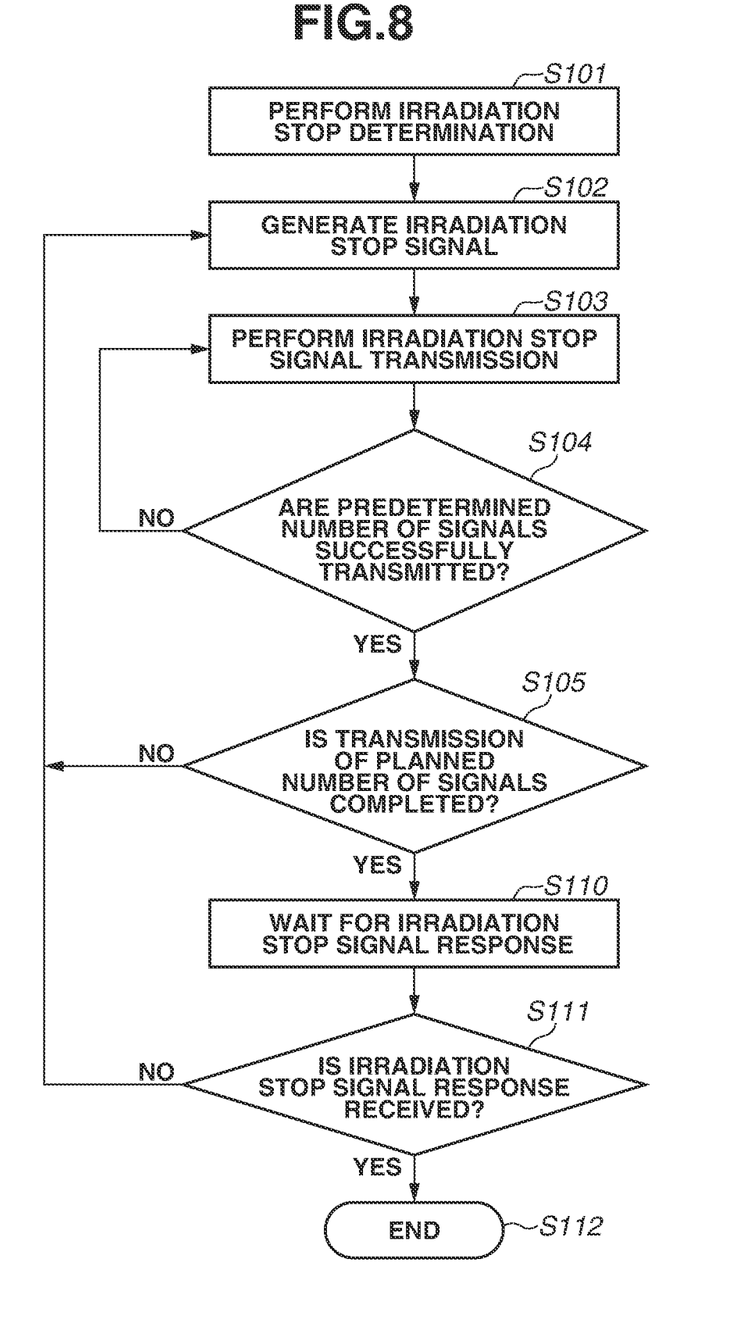
FIG. 8 is a diagram illustrating an example of a flow including re-transmission of an irradiation stop signal according to an exemplary embodiment.

Next, a case where the radiographic imaging apparatus 100 performs re-transmission using an irradiation stop signal response from the synchronization control apparatus 505 in an example of a flow of transmitting an irradiation stop signal will be described below with reference to FIG. 8. The process flow up to the determination of whether the transmission of the planned number of signals is completed in step S105 is similar to the flow in FIG. 7, and thus the description of those steps is omitted herein.

In step S110, the control unit 180 of the radiographic imaging apparatus 100 waits a predetermined period (first period) to check an irradiation stop signal response from the synchronization control apparatus 505. Then, in step S111, whether an irradiation stop signal response is received is checked. In a case where the irradiation stop signal response is received (YES in step S111), the processing proceeds to step S112 and exits the flowchart. In a case where no irradiation stop signal response is received (NO in step S111), the processing returns to step S102, and re-transmission of an irradiation stop signal is repeated at an interval of a predetermined period (second period). Additional signals of the irradiation stop signals to be re-transmitted can be updated as needed.

By setting the irradiation stop signal response waiting time in step S110 as appropriate based on an allowed communication delay time, the communication delay time is minimized while a load on communication traffic by an irradiation stop signal is suitably managed.

Figure 9:
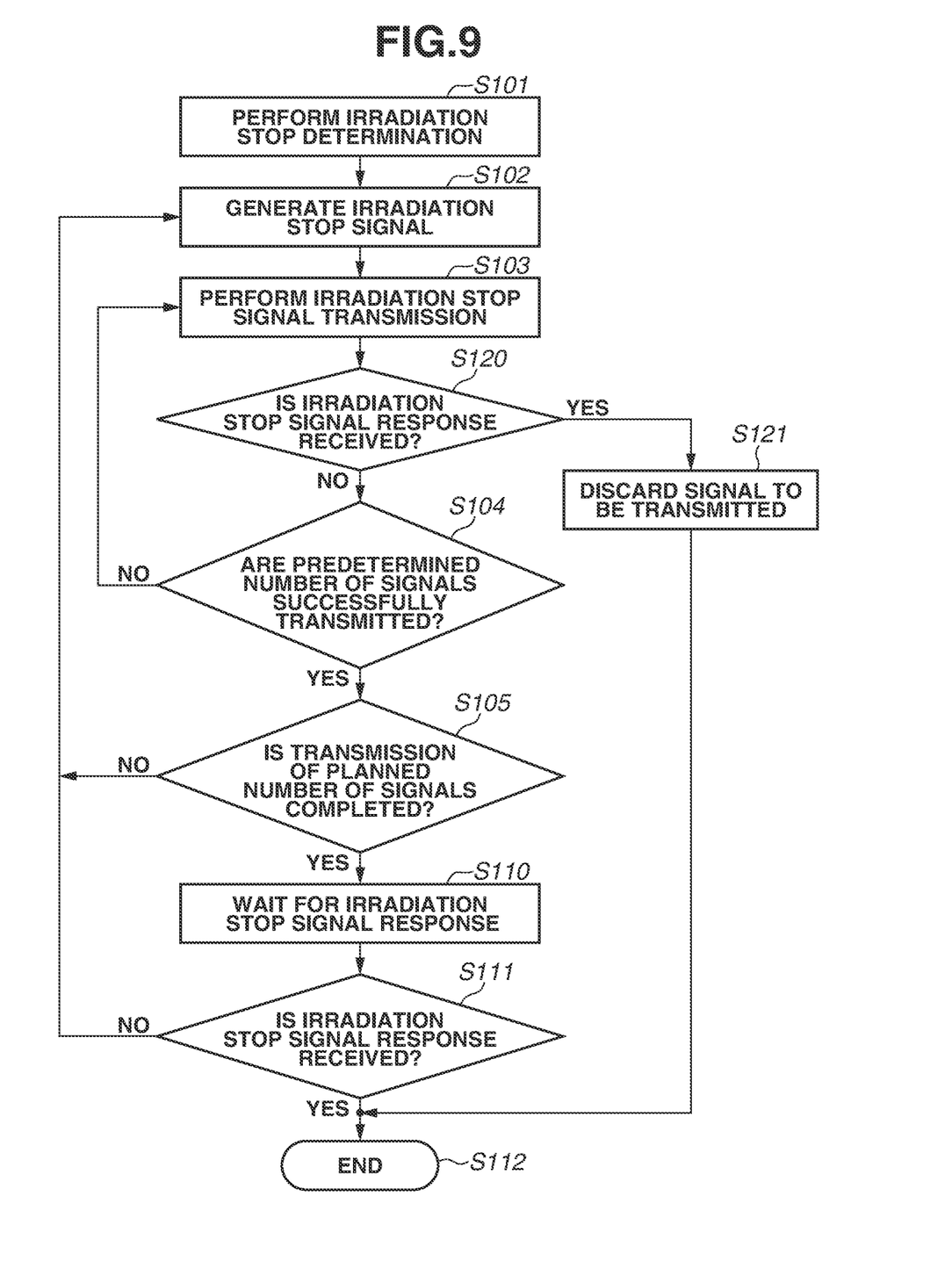
FIG. 9 is a diagram illustrating an example of a flow including discarding of an unnecessary irradiation stop signal according to an exemplary embodiment.

Next, a case where unnecessary signal transmission is reduced to reduce a load on communication traffic in an example of a flow of transmitting an irradiation stop signal by the radiographic imaging apparatus 100 will be described below with reference to FIG. 9. The process flow up to the irradiation stop signal transmission in step S103 is similar to the flows in FIGS. 7 and 8, and thus the description of those steps is omitted herein.

In step S120, whether an irradiation stop signal is received is checked. In a case where an irradiation stop signal is received (YES in step S120), the processing proceeds to step S121. In step S121, the control signal including the irradiation stop signal to be transmitted is discarded, and the control signal transmission ends. The foregoing operations enable reduction of unnecessary signal transmission, as well as reduction of a load on communication traffic.

An example of a sequence from the transmission of an irradiation stop signal from the communication unit 190 to the performance of irradiation stop control by the synchronization control apparatus 505 will be described below with reference to FIG. 10.

In step S201, the communication unit 190 transmits a plurality of control signals including an irradiation stop signal. In FIG. 10, a case where three pieces are transmitted is illustrated as an example. At this time, no response signal (ACK) is returned in a case where the access point 503 fails to receive a signal, so that the communication unit 190 transmits a control signal including an irradiation stop signal until a predetermined response signal (ACK) is acquired from the access point 503.

In step S202, the access point 503 transmits an irradiation stop signal to the synchronization control apparatus 505. At this time, a packet loss or a transmission delay can occur on the communication path including the access point 503 and the switching hub (not illustrated) to the synchronization control apparatus 505.

In step S203, the synchronization control apparatus 505 receives the irradiation stop signal and performs irradiation stop control on the radiation generation apparatus 506.

In step S204, the synchronization control apparatus 505 transmits an irradiation stop signal response to the communication unit 190 of the radiographic imaging apparatus 100 and notifies the radiographic imaging apparatus 100 of the performance of irradiation stop control.

In a case where an irradiation stop signal affected by a transmission delay is received after the irradiation stop control is performed in step S203, an additional signal such as an imaging ID is referred to. In a case where irradiation stop control is unnecessary, it is desirable not to perform irradiation stop control. At this time, while an irradiation stop signal response can be transmitted, it is not necessary for it to be transmitted.

For example, by transmitting an irradiation stop signal response together with information received with a delay, the radiographic imaging apparatus 100 acquires the delayed information, and the number of irradiation stop signals to be transmitted can be updated based on the information.

Figure 10:
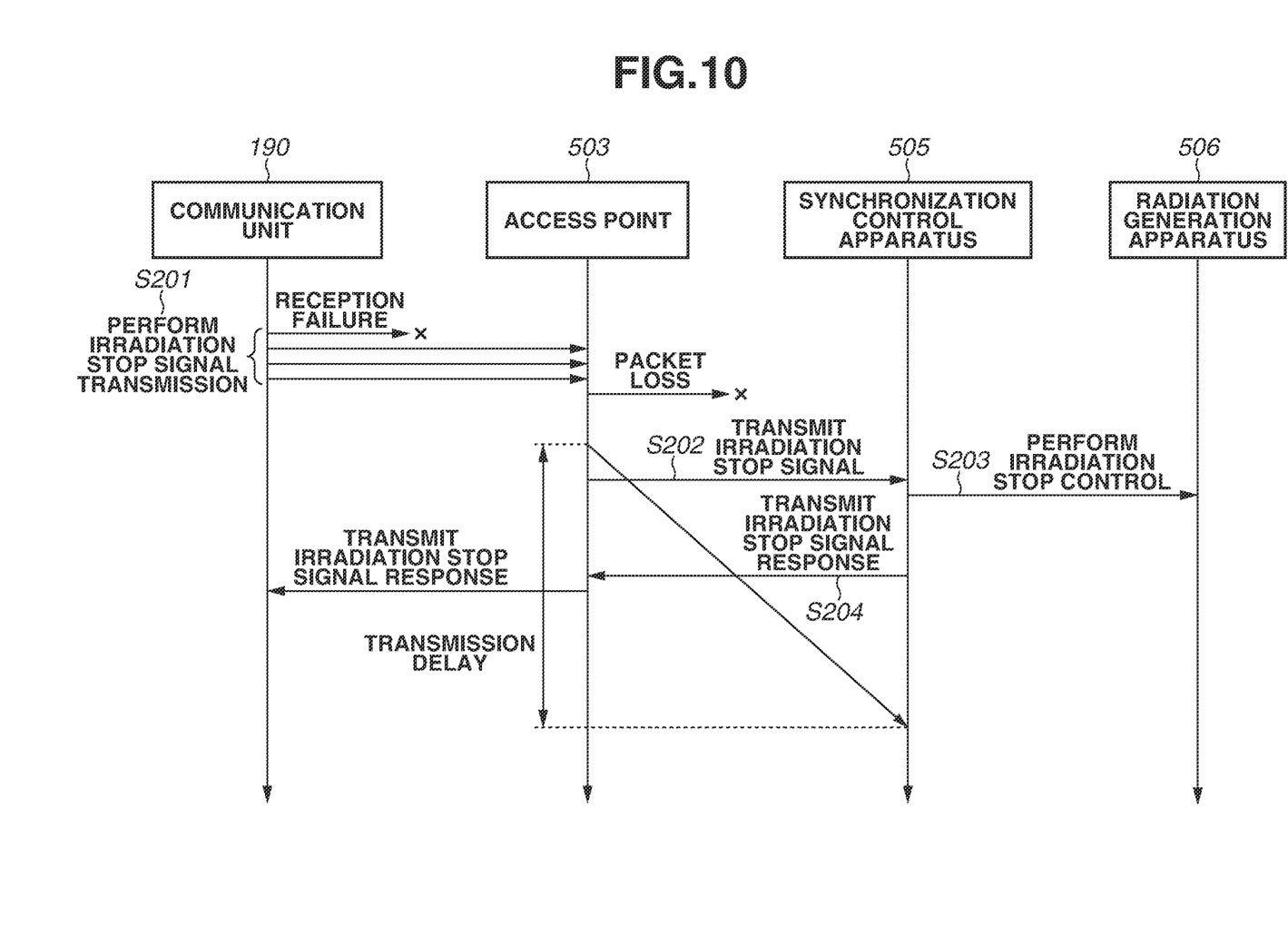
FIG. 10 is a diagram illustrating an example of a sequence of irradiation stop control of a radiographic imaging system according to an exemplary embodiment.

While the number of control signals including irradiation stop signals that are to be transmitted is three in FIG. 10, the number is not limited to three. For example, there can be a case where a communication device in which packets are accumulated until the accumulated packets reach a predetermined number of packets is on the communication path to the synchronization control apparatus 505, such as the access point 503 or the switching hub. In this case, a greater number of control signals to be transmitted is desirably set while a load on communication traffic is considered.

While details have been described above based on the exemplary embodiments, the present disclosure is not limited to the particular exemplary embodiments, and various forms within the spirit of the exemplary embodiments are also encompassed within the technical scope of the present disclosure. For example, simultaneous transmission can be performed using a plurality of communication units and/or a plurality of communication protocols. In another example, the communication unit 190 can use wired communication and can be connected to the synchronization control apparatus 505 via wires without the access point 503.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, these embodiments are not seen to be limiting. The scope of the following claims is to be accorded the broadest interpretation so as to encompass all such modifications and equivalent structures and functions.

This application claims the benefit of Japanese Patent Application No. 2022-103659, filed Jun. 28, 2022, which is hereby incorporated by reference herein in its entirety.

What is claimed is:

1. A radiographic imaging system comprising:
a control apparatus configured to control a radiation generation apparatus; and
a radiographic imaging apparatus including a sensor unit configured to detect radiation emitted from the radiation generation apparatus and a communication unit configured to transmit, to the control apparatus, an irradiation stop signal to stop the radiation generation apparatus from emitting radiation based on a dose of the radiation detected by the sensor unit,
wherein the communication unit transmits, to the control apparatus, a plurality of control signals as one set, each of the plurality of control signals including the irradiation stop signal, and
wherein the control apparatus stops generation of radiation from the radiation generation apparatus based on the plurality of control signals.

2. The radiographic imaging system according to claim 1, wherein each of the plurality of control signals includes an additional signal to be added to the irradiation stop signal.

3. The radiographic imaging system according to claim 2, wherein the additional signal of each of the plurality of control signals of one set is the same as the additional signal of each of the other control signals.

4. The radiographic imaging system according to claim 2, wherein the additional signal of each of the plurality of control signals of one set is different from the additional signal of each of the other control signals.

5. The radiographic imaging system according to claim 2, wherein the additional signal includes identification information indicating that each of the plurality of control signals includes the irradiation stop signal.

6. The radiographic imaging system according to claim 2, wherein the additional signal includes information indicating a transmission order of each of the plurality of control signals.

7. The radiographic imaging system according to claim 2, further comprising a calculation unit configured to calculate the dose,
wherein the additional signal includes information about the calculated dose.

8. The radiographic imaging system according to claim 2, wherein the additional signal includes time information or an imaging identifier to discriminate between a plurality of radiographic imaging operations.

9. The radiographic imaging system according to claim 2, wherein the additional signal includes dummy data.

10. The radiographic imaging system according to claim 1, further comprising an access point connected to the control apparatus and configured to receive a signal from the radiographic imaging apparatus.

11. The radiographic imaging system according to claim 1, wherein the number of control signals to be transmitted as one set by the communication unit is 1000 or less per transmission.

12. The radiographic imaging system according to claim 1, wherein in a case where no response is received from the control apparatus during a first period from the transmission of one set of the plurality of control signals, the communication unit repeats re-transmission of one set of the plurality of control signals at an interval of a second period.

13. The radiographic imaging system according to claim 1, wherein absent a request by the control apparatus, the communication unit does not transmit a signal to the control apparatus between a start of the emitting of the radiation by the radiation generation apparatus and an end of irradiation stop determination by the radiographic imaging apparatus.

14. The radiographic imaging system according to claim 1, wherein upon receipt of a response to the irradiation stop signal from the control apparatus, the communication unit discards a control signal scheduled to be transmitted after a time point of the receipt from among the plurality of control signals.

15. The radiographic imaging system according to claim 1, wherein the communication unit selects transmitting the plurality of control signals as one set in one transmission or only one control signal in one transmission.

16. The radiographic imaging system according to claim 1, wherein the control apparatus stops the generation of the radiation from the radiation generation apparatus based on a first control signal received from among the plurality of control signals transmitted as one set from the communication unit.

17. A radiographic imaging apparatus comprising:
a sensor unit configured to detect radiation emitted from a radiation generation apparatus; and
a communication unit configured to transmit an irradiation stop signal to stop the radiation generation apparatus from emitting radiation based on a dose of the radiation detected by the sensor unit,
wherein the communication unit transmits a plurality of control signals as one set, each of the plurality of control signals including the irradiation stop signal.

18. A radiographic imaging apparatus comprising:
a sensor unit configured to detect radiation emitted from a radiation generation apparatus; and
a communication unit configured to transmit an irradiation stop signal to stop the radiation generation apparatus from emitting radiation based on a dose of the radiation detected by the sensor unit,
wherein the communication unit transmits a control signal including the irradiation stop signal and an additional signal to be added to the irradiation stop signal.

19. A method for controlling a radiographic imaging apparatus including a sensor unit configured to detect radiation emitted from a radiation generation apparatus and a communication unit configured to transmit an irradiation stop signal to stop the radiation generation apparatus from emitting radiation based on a dose of the radiation detected by the sensor unit, the method comprising:
transmitting a plurality of control signals as one set, each of the plurality of control signals including the irradiation stop signal.

20. A non-transitory computer-readable storage medium storing a program for causing a computer to execute the method according to claim 19.

* * * * *